(12) United States Patent
Panizza (10) Patent No.: US 10,815,139 B2
(45) Date of Patent: Oct. 27, 2020

(54) MATERIAL FOR REDUCING THE CONTENTS OF POLLUTING AND/OR UNWANTED SUBSTANCES IN A LIQUID

(71) Applicant: ARCHIMEDE R&D S.R.L., Bologna (IT)

(72) Inventor: Lucio Panizza, Bologna (IT)

(73) Assignee: ARCHIMEDE R&D S.R.L., Bologna (IT)

( * ) Notice: Subject to any disclaimer, the term of this patent is extended or adjusted under 35 U.S.C. 154(b) by 0 days.

(21) Appl. No.: 16/335,172

(22) PCT Filed: Sep. 25, 2017

(86) PCT No.: PCT/IB2017/055804
§ 371 (c)(1),
(2) Date: Mar. 20, 2019

(87) PCT Pub. No.: WO2018/055588
PCT Pub. Date: Mar. 29, 2018

(65) Prior Publication Data
US 2019/0300408 A1    Oct. 3, 2019

(30) Foreign Application Priority Data

Sep. 23, 2016    (IT) ........................ 102016000095611

(51) Int. Cl.
*C02F 5/12*        (2006.01)
*B01J 31/00*       (2006.01)
(Continued)

(52) U.S. Cl.
CPC ............. *C02F 5/125* (2013.01); *B01J 31/003* (2013.01); *B01J 31/06* (2013.01); *C02F 1/42* (2013.01);
(Continued)

(58) Field of Classification Search
CPC .................. C02F 5/125; C02F 2101/10; C02F 2103/007; C02F 2103/08; C02F 2303/22;
(Continued)

(56) References Cited

U.S. PATENT DOCUMENTS

2005/0250193 A1    11/2005   Dziedzic et al.
2011/0127208 A1     6/2011   Sadowsky et al.
(Continued)

FOREIGN PATENT DOCUMENTS

CN            104071890 B      8/2015
WO    WO 2008/095057 A2       8/2008

OTHER PUBLICATIONS

International Search Report, issued in PCT/IB2017/055804, dated Jan. 18, 2018.
(Continued)

*Primary Examiner* — Fred Prince
(74) *Attorney, Agent, or Firm* — Tutunjian & Bitetto, P.C.

(57) ABSTRACT

A material for reducing the content of polluting and/or unwanted substances in a liquid includes at least one polymeric and/or inorganic base, suitable to be immersed in the liquid, having at least a surface, whereto is bonded at least one catalyst of the degradation reaction of inorganic salts in gaseous substances. The catalyst, whose function is to reduce the energy required for the activation of said reaction and to accelerate its progress, is an enzyme preferably selected among the lyase group, the hydrolase group and the oxidoreductase group.

17 Claims, 2 Drawing Sheets

(51) Int. Cl.
*C02F 1/42* (2006.01)
*C02F 3/10* (2006.01)
*C02F 3/34* (2006.01)
*C12N 11/02* (2006.01)
*B01J 31/06* (2006.01)
*C12N 9/00* (2006.01)
*C02F 5/10* (2006.01)
*C12N 9/14* (2006.01)
*C12N 9/88* (2006.01)
*C12N 11/08* (2020.01)
*C12N 9/02* (2006.01)
*C02F 101/10* (2006.01)
*C02F 103/00* (2006.01)
*C02F 103/08* (2006.01)
*C02F 103/02* (2006.01)

(52) U.S. Cl.
CPC .............. *C02F 3/104* (2013.01); *C02F 3/108* (2013.01); *C02F 3/342* (2013.01); *C02F 5/10* (2013.01); *C12N 9/004* (2013.01); *C12N 11/02* (2013.01); *C02F 2101/10* (2013.01); *C02F 2103/007* (2013.01); *C02F 2103/023* (2013.01); *C02F 2103/08* (2013.01); *C02F 2303/22* (2013.01); *C02F 2307/10* (2013.01); *C02F 2307/12* (2013.01); *C12N 9/0004* (2013.01); *C12N 9/14* (2013.01); *C12N 9/88* (2013.01); *C12N 11/08* (2013.01); *C12Y 402/01001* (2013.01); *Y02W 10/15* (2015.05)

(58) Field of Classification Search
CPC .... C02F 2307/10; C02F 2307/12; C02F 5/10; C02F 1/42; C02F 3/104; C02F 3/108; C02F 3/342; C02F 2103/023; B01J 31/06; B01J 31/003; Y02W 10/15; C12Y 402/01001; C12N 9/0004; C12N 9/14; C12N 9/88; C12N 11/08; C12N 11/02; C12N 9/004
USPC .................. 210/606, 632; 435/262, 262.5
See application file for complete search history.

(56) References Cited

U.S. PATENT DOCUMENTS

| | | | |
|---|---|---|---|
| 2014/0113346 A1* | 4/2014 | Ge | C12N 9/88 435/174 |
| 2014/0224721 A1 | 8/2014 | Panizza | |
| 2015/0252352 A1* | 9/2015 | Corgie | A62D 3/02 210/606 |

OTHER PUBLICATIONS

Written Opinion of the International Searching Authority, issued in PCT/IB2017/055804, dated Jan. 18, 2018.
Anonymous, "Dr Neu: Household Innovation—The simple and sustainable solution for cleaning and hygiene of the bathroom—Dr. Neu—L'innovazione e di casa", Sep. 4, 2016, XP055347815, Retrieved from the Internet: URL:http://www.doctorneu.com/en/2016/09/04/dr-neu-household-innovationthe-simple-and-sustainable-solution-for-cleaning-and-hygiene-of-the-bathroom/, total 4 pages.
Archimede: "New Sustainable Applications 1", Feb. 12, 2014, XP055347803, Retrieved from the Internet: URL:http://www.archimede-rd.it/wp-content/uploads/2013/03/ArchimedeRD_SoftenerDevice_EN.pdf, total 20 pages.

* cited by examiner

MATERIAL FOR REDUCING THE CONTENTS OF POLLUTING AND/OR UNWANTED SUBSTANCES IN A LIQUID

TECHNICAL FIELD OF THE INVENTION

The present invention relates to a material for reducing the contents of polluting and/or unwanted substances in a liquid.

The present invention further relates to a kit and a method for reducing the contents of polluting and/or unwanted substances in a liquid.

BACKGROUND ART

Nowadays, as is well known, the waters of natural and artificial bodies of water, lakes, rivers, seas and underground aquifers are used to various extents in industry. In addition, water already purified for human consumption still contains a high quantity of salts which can cause dysfunctions to the apparatuses in which it is used.

In particular, alkaline earth salts (calcium and magnesium) are major contributors to water hardness, i.e. the content of calcium and magnesium ions, in the form of phosphate salts, chlorides, nitrates, carbonates or hydrogen carbonates.

Therefore, primary water, because of the aforementioned impurities, are often subjected to treatments of different nature—for example mechanical, physical or chemical— suitable to make them meet the requirements of the uses for which they are intended.

Among unwanted substances (for example, among those that can be contained in potable water), a fundamental role is played by calcium, magnesium and sodium hydrogen carbonates, that is the inorganic calcium and magnesium salts.

As is well known, the presence in the water of calcium and magnesium carbonates, as well as of hydrogen carbonate salts, frequently determines the deposit of solid residues, normally defined as scale, which are a problem that today is very perceived in several areas of application.

More in detail, the water that flows through the conduits of water supply pipelines and that therefore is to be used for the most disparate purposes, including nutrition or for the operation of electrical appliances, contains various concentrations of metal ions such as the calcium ion, sodium ion, magnesium ion and/or ferrous ion. These ions are generally present in solution in water, in variable quantities, in the form of sulphates, chlorides, nitrates, carbonates or hydrogen carbonates; in particular environmental conditions, however, they can precipitate and, in the case of calcium and magnesium carbonates, but also of other insoluble mineral salts, form scale foulings.

Hence, as the hardness of the water, or of any other fluid, increases, as a result of the concentration of calcium, sodium and magnesium ions, in the form of phosphate salts, chlorides, nitrates, carbonates or hydrogen carbonates, so does the risk that the surfaces lapped by the water will be progressively affected by the formation of scale deposits of ever larger dimensions.

The foulings that are formed, therefore, on objects such as the walls of the conduits, of the electrical resistors, of the exchangers, and the like, of electrical appliances, boilers, etc., cause very high head losses, with consequent reductions in efficiency and reliability, and even heavy economic damages. These foulings also compromise the correct operation of the electrical resistors and of the exchangers, inasmuch as they cause greater energy needs to reach the required temperatures.

Moreover, the reduction of the unobstructed opening of the conduits, caused by scale, can cause blockages and permanent failures to the structures and/or apparatuses involved.

To reduce the hardness content of the water, and to avoid the unpleasant drawbacks due to the formation of scale, several solutions have been proposed over time, including the installation of apparatuses that operate on the water with physical and/or chemical treatments.

Among these systems, for example, are ionic exchange softeners, devices that utilise resins, i.e. artificially produced organic substances that have the peculiarities of having a mobile functional group, able to exchange ions between the resin and those dissolved in the water.

This system is quite effective but it does have several problems, among them corrosive phenomena that can cause the breakage of pipes, boilers and radiators; other problems are tied to the maintenance of the resins, which have to be treated periodically with bactericides and need to be regenerated with substances that, especially in the industry field, cause an increase in the pollution load of the sewerage.

Moreover, the aforesaid resins have a limited duration, very strictly tied to the quantity of unwanted substances present in the water.

This limited duration and the impossibility, in some cases, to reuse the materials, require a high replacement frequency, with the consequent severe impact on the environment and costs.

Another chemical treatment that can be carried out is the one with polyphosphates, and that involves the use of phosphates to form, together with calcium carbonate, a single stable macromolecule.

Since polyphosphates are toxic, as are also some waste products obtained with this treatment, this method is generally applied only to the treatment of water intended for technical consumption and, moreover, it has problems tied mainly to the difficulty of obtaining the correct dose of polyphosphates.

Moreover, it should be noted that the two processes described above, by means of ionic exchange and by means of polyphosphates, because of the significant potential for chemical pollution, should have, by law, a non-return valve upstream of the system, to avoid possible pollution of the urban water supply pipeline in case of pressure drops, thus causing additional costs and structural complications. Another known method to prevent the formation of scale is electrodialysis, which, however, is distinguished by very high installation and maintenance costs, and therefore is used only in industrial facilities.

In light of the difficulties highlighted above, concerning the removal of the polluting substances and above all of scale, it is noted that oftentimes the water made available through water supply pipeline to individuals has an even higher content of unwanted substances than the one allowed by regulations for nutritional use: in fact, the water dispensed from taps is excessively rich in pollutants, or otherwise in substances that give it an unpleasant taste.

This inevitably imposes the use of mineral waters on citizens, who thus often prefer them over tap water, with harmful consequences for the environment.

This, in fact, causes an increase in the production and use of single-use plastic bottles and hence an increase in oil consumption to manufacture them, in the consequent polluting emissions in the atmosphere (both by the extraction and refining plants and by the vehicles to transport the bottles), and lastly in the packaging materials to be disposed of in landfills.

In addition, the need to purchase mineral water implies a significant expenditure for the consumer, both due to the purchase of the water itself, and to a series of collateral costs: it is necessary to add the cost of the fuel for the travel by car to reach the place of sale, in addition to the costs in terms of time for the transport of heavy packages of four or six bottles, for stocking them at home and for consequently recycling the plastic bottles.

There are also indirect costs, which ultimately burden the consumer, and which are tied mostly to the innumerable trips of the motor vehicles that travel for hundreds of kilometres, to transport the empty bottles from the chemical industries that produce them to the companies that bottle mineral water (with consequent rise in pollution and traffic).

OBJECTS OF THE INVENTION

The technical aim of the present invention is to improve the state of the art.

Within such technical aim, one object of the present invention is to solve the problems described above, achieving a material able to reduce the content of unwanted substances, in water and in other fluids.

Another object of the present invention is to obtain a material able to reduce the hardness of water, defined by the concentration of calcium, sodium and magnesium ions in the form of sulphate salts, chlorides, nitrates, carbonates or hydrogen carbonates.

Yet another object of the present invention is to perfect a material able to reduce water hardness, and at the same time to purify the water itself from organic substances and/or bacteria and/or viruses and/or endotoxins.

Another object of the present invention is to achieve a material that makes it possible to meet the demand for consumer goods, for example bottled mineral water and distilled water for electrical appliances.

Another object of the present invention is to perfect a material that makes it possible to reduce the content of hydrogen carbonate and carbonate, and similar inorganic compounds, with limited environmental impact, and avoiding the discharge of pollutants in sewers and into the environment in general.

Still another object of the present invention is to make available a material that assures high operating reliability and a life span exceeding by at least 10% that of similar materials available on the market today, with the same water specifications and with the same operating procedures, including for example the contact time and quantity of material used.

This aim and these objects are all achieved by a material for reducing the content of polluting and/or unwanted substances in a liquid, according to attached claim 1.

The material according to the invention comprises at least one polymeric and/or inorganic base, suitable to be immersed in the aforesaid liquid, having at least a surface, onto which at least a catalyst is bonded, for the degradation reaction of inorganic salts in gaseous substances, said catalyst, responsible for the reduction of the energy required for the activation of said reaction and to accelerate its progress, being an enzyme preferably selected among the lyase group, the hydrolase group and the oxidoreductase group.

More specifically, in one embodiment of the invention the polymeric and/or inorganic base is made of polyamide.

In one embodiment of the invention, the enzyme is selected in the carbonic anhydrases group.

It is also an object of the invention to provide a kit for reducing the content of polluting and/or unwanted substances in a liquid, characterised in that it comprises at least a wrapper permeable to water and to the unwanted substances dissolved therein, to be immersed in the container of the liquid to be treated.

A plurality of bodies is contained within said wrapper a plurality of bodies, each comprising at least a portion achieved with the material according to the invention. The dependent claims refer to advantageous embodiments of the invention.

BRIEF DESCRIPTION OF THE DRAWINGS

These and further advantages shall be better understood by every person skilled in the art from the following description and from the accompanying drawings, provided purely by way of non-limiting example, in which.

EMBODIMENTS OF THE INVENTION

A preferred, but not exclusive, application is the use of the material according to the invention for the treatment of water bodies, i.e. masses of water having their own hydrological, chemical, physical and biological characteristics.

Hence, the definition of water bodies includes natural and artificial bodies of water, lakes, rivers, seas and underwater aquifers.

Still more specifically, the material according to the invention may be effectively employed to reduce the content of polluting, or otherwise unwanted substances, in the waters of water bodies listed above, in view of their use in various industrial sectors and/or before they are entered into the water pipelines intended for private or industrial users (or in any case before they reach these users).

In addition, a preferred, but not exclusive application of the material according to the invention is the one in the home environment for the use of water in bathroom fittings, in electrical appliances and for human and animal consumption.

An application of particular practical interest is the one inside containers containing a non-circulating, and hence still liquid, or eventually circulating in cyclical motion, but not changed or replaced except after a certain pre-determined time interval.

These containers can have any capacity, although one of the preferred applications is the one inside containers included within electrical appliances or the like.

Some examples, however nonlimiting, can be the coffee machine, the washing machine, or yet others.

The polluting and/or unwanted substances on which the material according to the invention can act comprise preferably, but not exclusively, inorganic compounds comprising oxide salts with generic formula of the type $M_W(XO_Z)_Y$.

In the aforesaid formula, M can be a metal ion, for example calcium ion, $Ca_{2+}$, magnesium ion $Mg_{2+}$, and ferrous ion $Fe_{2+}$, and/or a cationic entity.

Again with reference to the aforesaid formula, X can be an element preferably selected among carbon, nitrogen, sulphur, oxygen, phosphorous, boron, chlorine, fluorine, bromine, iodine and hydrogen.

Lastly, in the aforesaid formula W, Y and Z are such charges as to give the salt a neutral or balanced charge.

By way of example, therefore, the inorganic compounds on which the material according to the present invention can act can be inorganic salt of the type of carbonate salts, hydrogen carbonates, sulphates, magnesium, calcium, strontium nitrates, or they can be inorganic chlorine, sodium, magnesium, sulphur, calcium, potassium, bromine, carbon, strontium, boron, silicon, fluorine, argon, nitrogen and/or a mixture of such compounds.

In more detail, with particular reference to a preferred embodiment of the invention, the aforesaid inorganic compounds can consist of calcium and/or magnesium carbonates, sodium, calcium and magnesium hydrogen carbonates able, inter alia, to precipitate and form deposits, foulings, until forming layers of material known as scale.

It is specified, however, that the material according to the invention can also be used in application fields other than those described and/or for the treatment of different fluids, without departing from the scope of the invention claimed herein, if the specific needs make it possible of preferable.

According to an aspect of the present invention, the material for reducing the content of polluting substances comprises at least a polymeric base.

Said polymeric and/or inorganic base comprises at least a surface.

According to another aspect of the invention, at least the surface of the aforesaid polymeric and/or inorganic base supports at least a catalyst.

In particular, in an embodiment of the invention the aforesaid catalyst is a catalyst of the reaction of degradation of inorganic salt in gaseous substances.

For example, in an embodiment of the invention the aforesaid reaction can be the decarboxylation reaction and it can act for the conversion of inorganic salts into carbon dioxide (and water) according to the following reaction:

$$HCO_3^- + H^+ \rightarrow H_2O + CO_2$$

No matter what specific reaction takes place on the surface of the aforesaid polymeric base, the catalyst is suitable for reducing the energy required for its activation, and it is also able to accelerate its progress (thus allowing the reaction itself to take place in blander conditions and in a shorter time).

According to another aspect of the present invention, the aforesaid catalyst is an enzyme preferably selected from the lyase group, the hydrolase group and the oxidoreductase group.

No matter what the selected enzyme is, it is thus possible, thanks to it, to obtain the conversion of various polluting and/or unwanted substances, containing inorganic salts, in gaseous substances and water.

More specifically, according to a preferred, but not exclusive embodiment, the aforesaid catalyst is an enzyme selected in the lyase group.

Even more specifically, in an embodiment of the invention of particular practical interest, this enzyme, of the lyase group, is selected in the carbonic anhydrase sub-group.

The catalytic efficiency of an enzyme, also called turnover number, is defined as the number of molecules of substrate processed by an enzyme molecule in a time unit.

The turnover number for carbonic anhydrase is one of the highest known, i.e. approximately $10^5$-$10^6$ molecules processed per second.

The use of this enzyme in the material according to the invention is thus of particular interest for the objectives of the present invention.

The material according to the present invention comprises the aforesaid enzyme in a concentration preferably between 0.0001% and 30%, and still more preferably in a concentration between 0.005% and 1%, where all percentages refer to the total weight (as shall be better specified below).

The polymeric and/or inorganic base of the material according to the present invention, able to retain the catalyst physically and/or chemically, can be made of a material selected among polysulphone, cellulose acetate, cellulose acetate butyrate, cellulose nitrate, cellulose propionate, epoxides, polyamides, polyamide-imides, polyacrylonitrile, polybutene, polybutylene terephthalate, polycarbonate, polychlorotrifluoroethylene, poly diallyl phthalate, polyethylene, chlorinated polyethylene, polyetherimide, polyetherketone, polyether ether ketone, polyimide, polyisobutylene, polymethacrylimide, polymethylmethacrylate, poly-4-methylpentene-1, polyacetal, polyformaldehyde, polyoxymethylene, polyphenyl ether, polyphenylene oxide, polyurethane, chlorinated polyvinyl chloride, regenerated cellulose, silicones, polydimethylsiloxane, ABS.

In an embodiment of the invention of particular practical interest, mentioned for the purpose of illustrating the invention, but without limitation, the polymeric and/or inorganic base—able to retain the catalyst physically and/or chemically—comprises a plurality of synthetic fibres, which are preferably selected among polysulphone fibres, acrylic fibres, polyamide fibres, polyethylene fibres, polypropylene fibres, polyester fibres, polyurethane fibres, chlorovinylfibres, cellulose fibres and fluoro fibres, or inorganic substances such as resins, activated charcoal, or naturally derived substances, for example chitins, cellulose, etc.

The polymeric and/or inorganic base can comprise a combination of the materials listed above.

The polymeric and/or inorganic base of the material according to the present invention can have, in at least one portion thereof, a substantial lattice conformation, such as to define a plurality of cavities, with dimensions preferably, but not exclusively, between 1 nm and 20 nm.

These cavities have the peculiarity of having a cut-off preferably lower than, or equal to, 300 KDa.

The aforesaid cavities can be traversed, both in forced motion and in spontaneous motion, by water and/or by the other fluids to be treated, for the purpose of subjecting them to the action of the catalyst, associated with the aforementioned portion with substantial lattice configuration of the polymeric base.

According to an embodiment of the invention, of particular practical interest, the polymeric and/or inorganic base of the material is made of polyamide.

In an embodiment of the invention, the catalyst is covalently bonded to the surface of the polymeric and/or inorganic base.

In another embodiment of the invention, the catalyst is cross-linked to the surface of the polymeric and/or inorganic base.

The chemical bond between the surface of the polymeric and/or inorganic base and the catalyst is of the strong bond type.

This type of bond makes it possible to obtain the immobilisation of the catalyst to the polymeric and/or inorganic base in a stable manner, and this stability is highlighted by the prolonged duration of the effectiveness and of the activity of the catalyst itself.

Said prolonged duration manifests itself, with respect to other known technical solutions, with an increase in the ability to reduce unwanted substances in the treated fluid by more than 10%, in terms of volume of treated fluid (measured in litres).

When pipeline water, or another fluid, comes either into random or forced contact with the material of the present invention, a double advantageous effect is obtained, i.e. the removal of the inorganic substances and the purification from organic substances and/or bacteria and/or viruses.

A fundamental feature of the material according to the present invention is that it is effective even when it is merely placed in contact with the liquid to be treated, i.e. without a forced circulation of the liquid in such a way that it laps the surface of the material.

As stated, in an embodiment of the invention the base to which the catalyst is bonded can be inorganic.

In more detail, this definition means a base made of materials such as resins, sands, activated charcoal, chitins or other similar materials.

Figure 1:
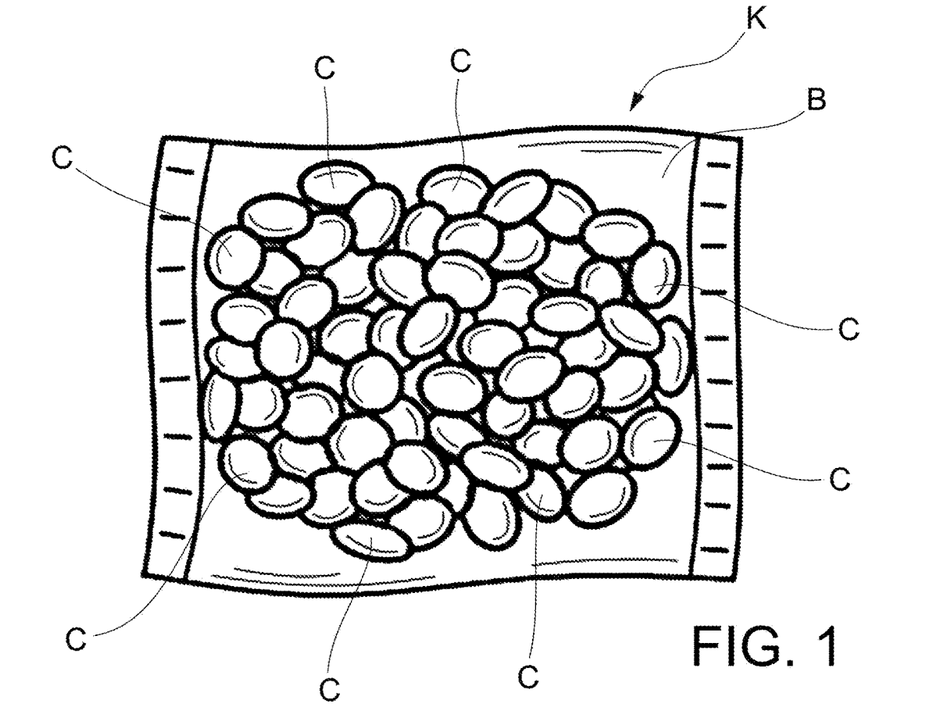
FIG. 1 is a schematic representation of a kit for reducing polluting substances to be immersed in the container of the liquid to be treated, comprising the material according to the present invention.

In an embodiment of particular practical interest of the present invention, schematically illustrated in FIG. 1, the material according to the present invention is inserted in sachets permeable to water and to the unwanted substances.

The present invention also relates to a kit K comprising at least a wrapper B permeable to water and to unwanted substances, in which at least a body C made of the aforesaid material is contained.

The wrapper B can be, for example, a sachet, or the like.

Said body C can be, for example, spherical, or substantially spherical.

Said body C comprises the aforesaid polymeric base.

Otherwise, in an embodiment of the invention the body C is entirely made of the aforesaid polymeric base.

The aforesaid body C can have any other shape suitable for the application.

The aforesaid body C can have dimensions of some millimetres and/or nanometres.

In an embodiment of the invention, the aforesaid body C can have dimensions between 0.01 mm and 10 mm.

This dimension refers, for example, to the average diameter if the body is substantially spherical, or otherwise the maximum enclosure size.

In an embodiment of the invention, the aforesaid body C can have dimensions between 0.1 μm and 5 mm.

In an embodiment of the invention of particular practical interest, the aforesaid body C can have, more specifically, dimensions between 2.5 mm and 3.5 mm.

Still more specifically, the aforesaid body C can have dimensions of approximately 3 mm.

The selection of this specific dimension (between 2.5 mm and 3.5, and more specifically approximately 3 mm) has been found to be advantageous from multiple viewpoints. Firstly, this specific dimension assures that an efficient immobilisation of the catalyst on the surface of the body C will be obtained.

An effective diffusion of the desired effect within the liquid to be treated is also obtained.

In other words, the surface of the body C having the aforesaid dimensions constitutes an optimal choice both from the viewpoint of the quantity of the immobilised catalyst, and from the viewpoint of the efficiency of the treatment of the fluid by the catalyst itself.

In fact the available surface is sufficiently extended to immobilise the necessary quantity of catalyst; at the same time, the body C has optimal dimensions to obtain the effective treatment of liquids within containers used in the most common applications, as shall be better clarified below.

The applicant, after carrying out tests with bodies C of different dimensions, determined that the optimal results are obtained using a body C having dimensions of approximately 3 mm, and it instead obtained definitely less interesting results with bodies C having dimensions below 1 mm.

One of the disadvantages when using bodies C with dimensions below 1 mm derives from the fact that the immobilisation efficiency of the enzyme and its related activity are less effective; this can be caused by the dimensions of the enzyme; enzymes are known to be macromolecules which, if bonded in excessively small volumes, can modify their steric conformation, partially or totally inhibiting the access to the active site, responsible for the catalysis reaction.

In an embodiment of the invention of particular practical interest, the kit K comprises a wrapper B comprising a plurality of the aforesaid bodies C.

For example, sachets B containing a certain number of bodies C can be made, thereby obtaining a kit K having a pre-set weight (e.g., a few tens of grams).

Naturally, the dimensions of the kit K (and hence its weight) must be adequate for its specific application.

Such a wrapper B can be inserted in the container where the liquid to be treated is present, and the random contact between the unwanted substances and the material is such that the reduction of the unwanted substances becomes readily apparent.

The dimensions of the kit K can thus be determined, for example, in relation to the capacity of the container that contains the liquid to be treated.

In this regard, it should be observed that the optimal dimensions of the bodies C, indicated above (i.e. between 2.5 mm and 3.5 mm, and more specifically approximately 3 mm) provide satisfactory results even within the use in a kit K comprising a plurality of bodies C contained within a same wrapper B.

In fact—and in comparison with the alternative of bodies C with dimensions smaller than 1 mm—the selected solution has a wider surface in contact with the liquid; the reason for this is that excessively small and light bodies C (hence, with dimensions smaller than 1 mm), after immerging the kit K in the liquid, albeit contained within a wrapper B, could tend to group/cluster in an inconsistent manner, especially at determined areas of the container in which the kit K is immersed (for example at the angles of the container, or at irregular surfaces, niches, holes, grooves, and the like).

This phenomenon—as can be intuitively understood— considerably limits the contact surface of the bodies C, contained in the wrapper B, with the liquid to be treated, and hence the active and effective surface of the catalyst.

This phenomenon is extremely reduced with bodies C with greater dimension (of approximately 3 mm), because the tendency to form irregular groupings at determined areas of the container of the liquid is lower.

At the same time, bodies C of larger dimensions (e.g. above 5 mm, and up to 10 mm), become excessively heavy (the weight increases with the cube of the radius) and bulky, so that their use can be inconvenient, if not impossible, in applications in which the container of the liquid is relatively small.

In addition, bodies with excessively high volumes make the probability of contact between the liquid and the surface statistically lower, thus reducing the effectiveness of the invention.

When the kit K is introduced in the liquid to be treated, the gas produced by the catalysed reaction moves away from the material, while the unwanted substances (especially inorganic salts in ionic form) come in contact, according to the principles of ion diffusion and of equilibrium of electrical potential in solutions, with the surface of the polymeric and/or inorganic base of the material itself, enabling the latter to continue its action of reducing the content of the aforesaid unwanted substances.

Therefore, it is specified that the aforementioned percentages, relating to the preferred concentrations of enzymes, refer to the total weight of the polymeric and/or inorganic base (according to the specific embodiment selected).

As mentioned previously, in an embodiment of the invention the immobilisation of the catalyst on the surface of the polymeric base can be of the covalent type; the catalyst is then bonded directly to the polymeric base itself.

In another embodiment of the invention, the immobilisation of the catalyst on the surface of the polymeric and/or inorganic base can be of the crosslinking type.

In more detail, chemical bonds are formed between the molecules of the catalyst, which realise a crosslinking: this crosslinking envelopes the polymeric and/or inorganic base in a highly stable manner, remaining active with respect to the reduction of unwanted substances in water or in other fluids.

If the polymeric and/or inorganic base is comprised in the body C, i.e. it constitutes at least one portion of the body C, the crosslinking can involve the entire body C, or the portion thereof comprising the aforesaid polymeric base.

According to the present invention, multiple modes of immobilisation of the catalyst on the surface of the polymeric and/or inorganic base (among those mentioned above, or even others) can be variously combined with each other, without particular limitations.

Whatever it is the selected mode of immobilisation of the catalyst on the surface of the polymeric and/or inorganic base of the material, the release of the catalyst into the environment is effectively contrasted and/or eliminated, in such a way as to reduce or eliminate the accidental, and unwelcome, release of catalyst in water or in the other treated fluids.

In another embodiment of the invention, the wrapper B of the kit K can consist of at least a container suitable to be traversed by the liquid to be treated.

In more detail, in this embodiment of the invention the wrapper B can be inserted along a pipe in such a way that the flow of water traverses it, and hence comes into even random contact with the bodies C contained therein.

The operation of the material according to the invention is thus as follows.

Subjecting water, or another fluid to be treated, to random or forced contact with the material according to the invention, and hence with the catalyst associated with the surface of its polymeric base, it is possible to obtain the conversion of the salts into non-polluting gaseous substances (for example carbon dioxide) achieving in fact the set purpose as a result of the action of the enzyme which, as stated, in some embodiment of the invention constitutes the catalyst included in the material itself.

As stated, the enzyme is able to reduce the quantity of energy required for the activation of the aforesaid reaction, and hence to accelerate its progress, thus enabling the reaction itself to take place in blander conditions and in a shorter time.

By thus promoting the activation and the progress of the reaction, it is possible to obtain in a practical and economical manner, in the treated liquid, the conversion of large quantities of polluting, or otherwise unwanted substances: in the case of pipeline water, in which said unwanted substances comprise inorganic salts that have the general formula set out above, the supply of appropriately treated water is thus assured to different types of users.

The enzyme is able to convert these compounds, e.g. carbonate salts or hydrogen carbonate salts, into carbon dioxide, and this makes it possible to achieve the set purpose of reducing the concentration of unwanted and/or polluting substances.

This result is obtained without causing any harmful effects for humans and/or the environment: in fact, the enzyme selected is a totally natural, biocompatible and biodegradable biological element, consisting of a single natural protein molecule.

As stated, it must be added that the effective immobilisation of the catalyst on the surface of the polymeric and/or inorganic base prevents the catalyst from being released in the treated liquid in an uncontrolled manner.

The material according to the invention, therefore, does not release toxic or harmful elements for humans and/or for the environment, or at least releases them to a markedly lower extent than other technical solutions known for the purpose.

Consumption and discharge into nature of harmful substances for human and environmental health is thus reduced, thereby avoiding sewage pollution phenomena.

According to a preferred, but not exclusive embodiment of the invention, the manufacturing of the polymeric and/or inorganic base comprising polyamide fibres makes it possible to fully exploit the peculiarities of such fibres, i.e. in particular the fact that they are made of an amorphous, high performance thermoplastic resin. Polyamide is a material that has interesting properties such as high tensile strength, high temperature in continuous use and excellent dimensional stability.

In addition to the low absorption of water, polyamide also has high resistance to electrolysis, which enables it to be used reliably even in applications in contact with hot water.

Polyamide can be sterilised in several ways, therefore it is suitable for contact with foods and potable water, and it has high chemical and biological resistance (for example, it can withstand being attacked by molds).

The characteristics of polyamide, described above, make it suitable for contact with liquids intended for human and animal consumption, fields where it is currently widely used.

Two examples of tests for verifying the activity of the catalyst bonded to the surface of the polymeric and/or inorganic base of the material according to the present invention are described in detail below.

Example 1

The tests refer to the activity of the polymeric polyamidic base to which the enzyme is covalently bonded, in particular an enzyme of the carbonic anhydrase class.

The purpose of the test is to verify the activity of degradation of the polymeric base, to which the enzyme is bonded covalently, towards inorganic salts such as carbonate salts and/or bicarbonate salts dissolved in water.

The tests comprised 2 successive steps:
1) covalent immobilisation of the carbonic anhydrase enzyme on the polymeric polyamidic base, and characterisation of the immobilisation efficiency;
2) determination of the degradation activity of the polymeric base referred to in point 1 towards carbonate and/or bicarbonate salts.

All samples were analysed with the electrode sensitive to $CO_2$, so as to establish the activity of the immobilised enzyme and that of the residual one. A specific feature of the invention is the degradation of the carbonate and/or bicarbonate salts and their consequent conversion into $CO_2$.

The activity essays were carried out at pH=7.6 and ambient temperature.

The invention has the specific feature of favouring, in a non-obvious way, the transformation of said salts into $CO_2$, through a particular catalytic activity of carbonic anhydrase.

Step 1—Immobilisation by Introduction of a Single Bond
1) Add 100 g of pre-treated Polyamide (3 mm bodies) to 784 mL of Sodium Phosphate 100 mM pH 8.
2) Add 16 mL of glutaraldehyde 25% to the 784 mL of Sodium Phosphate (final volume 800 mL, final glutaraldehyde concentration: 0.5%).
3) Add Polyamide and derivatise for 1 h at 20° C.
4) Transfer the treated and derivatised Polyamide in the enzyme solution and leave under agitation for 17 hours at 20° C.
5) Carry out two washes with 1 L of double-distilled water.
6) Let the Polyamide dry under a hood for approximately 15 h.

Results of Step 1

During the immobilisation process, two samples of enzymes in solution were drawn: the first sample represents the enzyme solution at the initial moment of the immobilisation process, while the second sample represents the residual enzyme solution at the end of the immobilisation (after 17 h). This sampling was made for every immobilisation experiment; in parallel, at the end of the immobilisation process a portion of the Polyamide containing the immobilised enzyme was preserved.

The ten samples containing the residual enzyme in solution were analysed with the Bradford method, to determine its total protein concentration. Each sample was double analysed.

In the case of the four lots of Polyamide produced by single bond immobilisation, the initial enzyme concentration was found to be equal to 3.6±0.3 mg/mL, while the residual enzyme concentration at the end of the immobilisation process was found to be equal to 3.2±0.13 mg/mL.

The estimated immobilisation efficiency, based on the activity data, was found to be 2.1±1.4%.

Step 2—Activity Test of the Polymeric Polyamide Base to which the Carbonic Anhydrase Enzyme is Covalently Bonded.

The purpose of this experiment is to verify the—non-obvious—activity of the carbonic anhydrase enzyme, if immobilised on polymeric support, in the catalysis of the reaction of degradation of carbonate and/or bicarbonate salts dissolved in water.

The activity tests were conducted at ambient temperature and at pH below 9, because these were found to be the most effective operating parameters.

Protocol:
1) Prepare 200 mL of sodium citrate 150 mM pH 5 (1×)
2) Prepare 100 mL of Tris-HCl 400 mM pH 7.6 (2×)
3) Prepare 5 mL of zinc sulphate 1 mM (1000×)
4) Prepare 10 mL of sodium bicarbonate 50 mM (10×).
5) Determine the calibration curve with 0.050, 0.5, and 5 mM of sodium bicarbonate; the analysis is carried out taking the solution under agitation and waiting approximately 20 min to reach a constant concentration of carbon dioxide.

Solutions to be Prepared:
Blank: 30 mL of sodium citrate pH 5.
Sample 0.05 mM: 30 μL sodium bicarbonate 50 mM+30 mL of Sodium Citrate pH 5.
Sample 0.05 mM: 30 μL sodium bicarbonate 50 mM+30 mL of Sodium Citrate pH 5.
Sample 5 mM: 3 mL sodium bicarbonate 50 mM+27 mL of Sodium Citrate pH 5.

6) Analysis of the Polyamide Containing Immobilised Carbonic Anhydrase:
4.5 mL of double-distilled water
4.5 mL Tris-HCl 400 mM
10 μL of zinc sulphate 1 mM
0.74 mg of Polyamide
Carry out a measurement for 20 s, then add 1 mL of sodium bicarbonate 50 mM.

Results of Step 2

All samples were analysed with the electrode sensitive to $CO_2$, so as to establish the activity of the immobilised enzyme and that of the residual one. In the case of the samples immobilised by single bond, the mean activity observed in Polyamide was found to be equal to 37.9±12.40 μg $CO_2$/l·s.

Example 2

The tests refer to the activity of the Polyamide polymeric base around which the enzyme is crosslinked, in particular an enzyme in the class of the carbonic anhydrase.

The purpose of the test is to verify the enzymatic activity of the polymeric base, to which the enzyme is externally crosslinked, towards inorganic salts such as carbonate salts and/or bicarbonate salts dissolved in water.

In this case, too, the tests comprised 2 successive steps:
1) covalent immobilisation of the carbonic anhydrase enzyme on the polymeric polyamidic base, and characterisation of the immobilisation efficiency;
2) determination of the degradation activity of the polymeric base referred to in point 1 towards carbonate and/or bicarbonate salts.

All samples were analysed with the electrode sensitive to $CO_2$, so as to establish the activity of the immobilised enzyme and that of the residual one.

The activity essays were carried out at pH=7.6 and ambient temperature.

Phase 1—Immobilisation by Crosslinking
1) Dissolve 8 g of enzyme in 400 mL of sodium phosphate dibasic 100 mM pH 8, leaving under agitation for approximately 1 h (solution 1).
2) Add 16 mL of glutaraldehyde 25% in 400 mL of sodium phosphate dibasic 100 mM pH 8 and allow to disperse for 1 min (solution 2).
3) Add 100 g of Polyamide in solution 2.
4) Transfer solution 1 into solution 2.
5) Incubate the Polyamide for 17 h at 20° C. under agitation.
6) Carry out the appropriate washes
7) Let the treated Polyamide dry.

Results of Step 1

During the immobilisation process, two samples of enzymes in solution were drawn: the first sample represents the enzyme solution at the initial moment of the immobilisation process, while the second sample represents the residual enzyme solution at the end of the immobilisation (after 17 h). This sampling was made for every immobilisation experiment; in parallel, at the end of the immobilisation process a portion of the polyamide containing the immobilised enzyme was preserved.

The ten samples containing the residual enzyme in solution were analysed with the Bradford method, to determine its total protein concentration. Each sample was double analysed.

The immobilisation efficiency by crosslinking, estimated based on the activity data (considering the total residual and immobilised activity) was found to be equal to 2.4%.

Step 2—Activity Test of the Polymeric Polyamide Base to which the Carbonic Anhydrase Enzyme is Crosslinked.

The purpose of this experiment is to verify the—nonobvious—activity of the carbonic anhydrase enzyme, if immobilised by crosslinking on the polymeric base, in the catalysis of the degradation reaction of carbonate and/or bicarbonate salts dissolved in water.

The activity tests were conducted at ambient temperature and at pH below 9, because these were found to be the most effective operating parameters.

Protocol:
1) Prepare 200 mL of sodium citrate 150 mM pH 5 (1×)
2) Prepare 100 mL of Tris-HCl400 mM pH 7.6 (2×)
3) Prepare 5 mL of zinc sulphate 1 mM (1000×)
4) Prepare 10 mL of sodium bicarbonate 50 mM (10×).
5) Determine the calibration curve with 0.050, 0.5, and 5 mM of sodium bicarbonate; the analysis is carried out taking the solution under agitation and waiting approximately 20 min to reach a constant concentration of carbon dioxide.

Solutions to be Prepared:
Blank: 30 mL of sodium citrate pH 5.
Sample 0.05 mM: 30 µL sodium bicarbonate 50 mM+30 mL of Sodium Citrate pH 5.
Sample 0.5 mM: 300 µL sodium bicarbonate 50 mM+30 mL of sodium citrate pH 5.
Sample 5 mM: 3 mL sodium bicarbonate 50 mM+27 mL of sodium citrate pH 5.

6) Analysis of the Polyamide Containing Immobilised Carbonic Anhydrase:
4.5 mL of double-distilled water
4.5 mL Tris-HCl400 mM
10 µL of zinc sulphate 1 mM
0.74 mg of Polyamide
Carry out a measurement for 20 s, then add 1 mL of sodium bicarbonate 50 mM.

Results of Step 2

All samples were analysed with the electrode sensitive to $CO_2$, so as to establish the activity of the immobilised enzyme and that of the residual one.

In the case of the samples immobilised by crosslinking, the mean activity observed in Polyamide was found to be equal to 14 µg $CO_2$/l·s.

Example 3

Example 3 describes the activity tests of the enzyme crosslinked on a base of commercial ionic exchange resins.

Both step 1—immobilisation, and step 2—test of enzymatic activity in the degradation of inorganic hydrogen carbonate and/or carbonate inorganic salts are conducted in the same conditions described in example 2.

In the case of the samples immobilised by crosslinking, the mean activity observed in Polyamide was found to be equal to 10 µg $CO_2$/l·s.

The material according to the invention can be used for different applications according to specific requirements; for example, it is provided to subject water to be made potable to the action of the material according to the invention, because the action of the enzyme allows to effectively remove scale deposits, and more in general to reduce water hardness, defined as the concentration of calcium and magnesium ions in the form of sulphate salts, chlorides, nitrates, carbonates and hydrogen carbonates.

The water thus treated can be effectively sent to user devices, which can thus receive, at low costs and in a practical manner, water free of substances that are polluting, or otherwise such as to give an unpleasant flavour, making it absolutely suitable for use for nutrition purposes, for use as demineralised water and also to be drunk.

The choice of using an enzyme, such as one among those indicated above, makes it possible to use a highly specific catalyst, since the protein envelope of the enzyme itself creates a pocket, known as active site, able to house only the accessible substrate molecules.

Moreover, unlike other elements the enzyme carries out a gradual reduction of the hardness of the water, maintaining in solution a percentage of salts and/or ions (for example the $Ca_2^+$ ion) useful for human health, thus making absolutely interesting the use of the material according to the invention for treating water intended for private users and/or for nutrition uses.

In addition, the high catalytic efficiency makes it possible to keep low the concentration of the enzyme within the material according to the invention, in order to contain the costs necessary for its manufacturing and marketing.

In this way, a competitive solution is obtained from the economic viewpoint, with respect to apparatuses already present on the market.

Lastly—a very important fact—since the enzyme is a catalyst, the latter has the additional peculiarity of remaining unaltered at the end of the reaction it catalyses, thus making its use possible for a varied number of catalytic cycles, with additional advantages from the economic viewpoint.

Proof of such effectiveness, which can remain unaltered over time, it has been demonstrated that the material according to the invention has a prolonged efficiency above 10% (considering the volume of treated water, in litres) in the reduction of unwanted substances, with respect to other technical solutions present on the market.

More specifically, an effectiveness test was carried out on the material according to the present invention employed—as described above—in the form of a kit K comprising a wrapper B permeable to water, containing a plurality of bodies C, each comprising the aforesaid polymeric base to which the catalyst (enzyme) is associated.

The effectiveness test provides for the use of a kit K comprising a sachet B containing an amount by weight of 15 g of the aforesaid bodies C, in one litre of treated water.

Initially, the treated water has a hardness of 45°f, equal to 586 mg/l of sodium bicarbonate.

In performing the test, the material according to the invention is allowed to act without agitation.

In addition, it is allowed to act without creating liquid displacements or artificial currents to lap the surfaces of the polymeric base.

Samples of the treated water were drawn at predetermined times: in particular, samples were drawn at 10, 30, 45 minutes, and subsequently at 1, 2, 4, 8, 24, 48 hours.

The following table shows the outcomes of the aforesaid samplings, and the corresponding percentage reduction of the content of sodium bicarbonate in the treated volume of water. The values were determined according to the method ASTM D513.

TABLE 1

Percentage reduction of bicarbonate in the treated volume of water.

| Time (min), 1 sachet | Bicarbonate, mg/l | Difference % |
|---|---|---|
| 0 | 590.59 | — |
| 10 | 571.88 | −3.17% |
| 30 | 538.38 | −8.84% |
| 45 | 524.13 | −11.25% |
| 60 | 497.22 | −15.81% |
| 120 | 518.34 | −12.23% |
| 240 | 527.03 | −10.76% |
| 480 | 511.91 | −13.32% |
| 900 | 226.55 | −61.64% |
| 1440 | 190.24 | −67.79% |
| 2880 | 150.09 | −74.59% |

Figure 2:
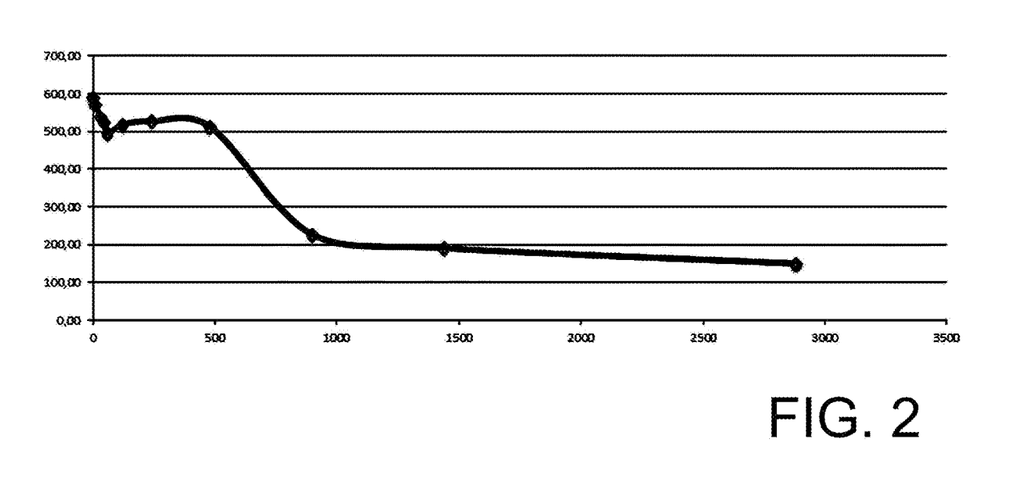
FIG. 2 is a chart, relating to a test carried out, which shows the reduction, in percentage terms, of an unwanted substance (carbonate and hydrogen carbonate salts), as a function of time, in a volume of liquid treated with the material according to the present invention.

The same results are also shown in graphic form in FIG. 2.

Figure 3:
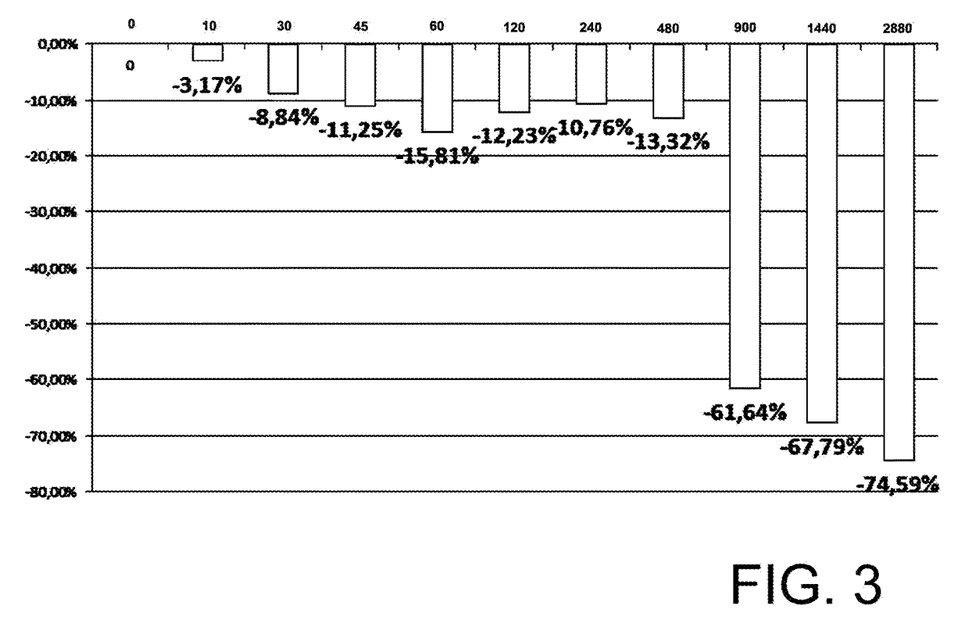
FIG. 3 is a histogram showing the reduction of unwanted substance (carbonate and hydrogen carbonate salts), in percentage terms and as a function of time, in the test of FIG. 2.

FIG. 3, instead, more explicitly shows the reduction in percentage terms of bicarbonate over time, in the treated volume of water.

As can be observed, approximately 30 minutes after the start of the treatment the activity of the material according to the invention begins in the reduction of the bicarbonates-carbonates present in the treated volume of water.

After approximately 45 minutes from the start, the activity becomes readily apparent.

48 hours after the start of the treatment, a reduction by nearly 75% in bicarbonates-carbonates was obtained.

Another important aspect of the present invention is that the reduction of the unwanted substances (in this case, bicarbonates-carbonates) is kept constant over time even for high volumes of liquid treated, i.e. it does not exhaust its effectiveness as the volume of treated liquid progressively increases.

This result cannot be obtained with the prior art technical solutions currently available on the market, such as ion-exchange resins.

It is also known that enzymes have long-term activity problems: these catalysts are commonly susceptible to inactivation by contaminants. The present invention instead is effective in real application conditions. The maintained effectiveness in the degradation of the salts is highlighted in table 3, which shows how the enzymatic activity allows after 200 lt to reduce the content of unwanted substances efficiently.

With particular reference to the latter substances, and as clarified previously, a specific comparison test was also carried out between the water treatment at the inlet to a coffee machine, respectively, with an ion-exchange resin and with the material according to the present invention.

In particular, 400 g of ion-exchange resin were used in one case, and 400 g of material according to the present invention were used in the other case.

The tables that follow show the results of the comparative tests, which assessed the effectiveness of the tested materials as the volume of treated water increases.

Table 2 shows the results relating to the ion-exchange resin; table 3 shows the results relating to the material of the present invention.

TABLE 2

Ion-exchange resin
(The values were determined through EDTA titration)

| Treated water (l) | $CaCO_3$ removed (mg/l) |
|---|---|
| 1 | 1539.4 |
| 5 | 668.2666667 |
| 20 | 417.6666667 |
| 40 | 286.4 |
| 50 | 334.1333333 |

TABLE 3

Material according to the invention
(The values were determined according to the method ASTM D513).

| Treated water (l) | $CaCO_3$ removed (mg/l) |
|---|---|
| 1 | 600 |
| 100 | 800 |
| 200 | 933.33 |

Figure 4:
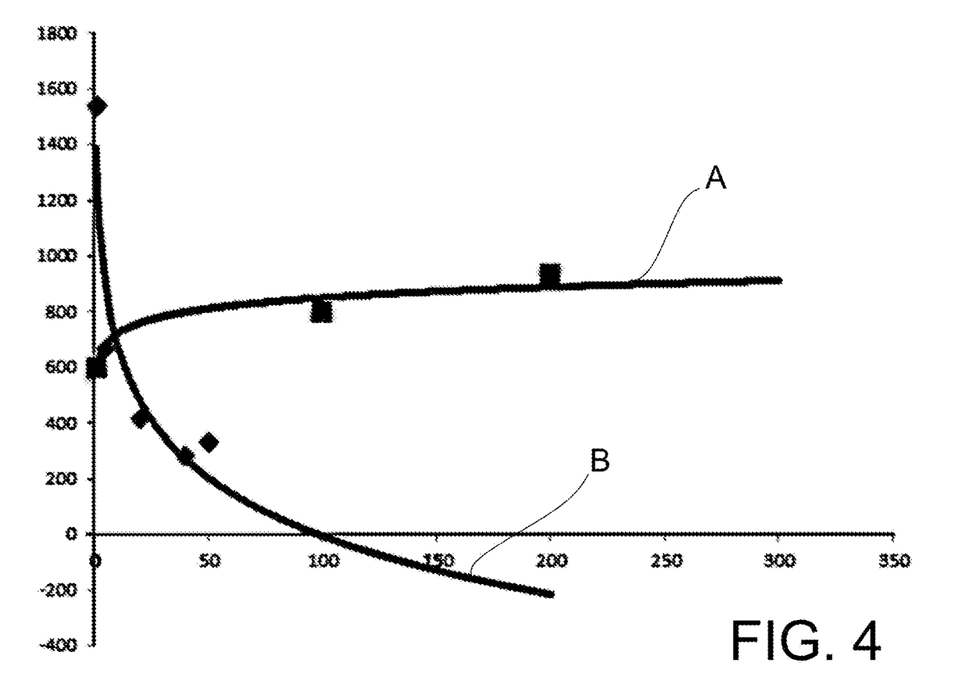
FIG. 4 is a chart relating to a comparative test of reduction of unwanted substances, in which the results obtained with the material according to the present invention and with an ionic exchange resin are compared.

The results shown in the aforesaid tables 2, 3 are also represented graphically in FIG. 4, for better comparison.

In particular, curve A refers to the material according to the invention, while curve B refers to the ion-exchange resin.

As can be observed, the effectiveness in the removal of the unwanted substances (in this case, $CaCO_3$) of the material according to the present invention remains absolutely unaltered over time, i.e. as the volume of liquid treated progressively increases, while the effectiveness of the ion-exchange resin is very high for relatively small volumes of water, but it decreases very suddenly over time: after a certain treated volume of water, the ion-exchange resin becomes substantially ineffective, and it must be fully replaced, with consequent higher operating costs.

On the contrary, as it has been shown, the material according to the present invention does not require any regeneration intervention: hence, the savings in economic terms are readily apparent.

It should also be stressed that the material according to the invention makes it possible to obtain a focused removal of a determined substance, without ion exchange phenomena which instead occur for resin and which could be unwanted, as a result of the release of ions from the resin itself.

Additional tests were also carried out to determine the average values of reduction of the hardness of the water treated using the material according to the present invention, in various possible practical applications.

A first test (documented in table 4 below) was carried out making a filtering element, containing approximately 7 kg of material according to the present invention, connected to the water supply pipeline, to measure the reduction of the scale with different water flow rates.

TABLE 4

First hardness reduction test, water supply pipeline
(The values were determined according to the method ASTM D513)

| Sample | Hardness (° f.) | Scale reduction (%) |
|---|---|---|
| Pipeline water | 21 | — |
| Filter outlet flow rate 0.23 l/min | 12 | 43 |

TABLE 4-continued

First hardness reduction test, water supply pipeline
(The values were determined according to the method ASTM D513)

| Sample | Hardness (° f.) | Scale reduction (%) |
|---|---|---|
| Filter outlet flow rate 0.6 l/min | 14 | 33 |
| Filter outlet flow rate 8 l/min | 16 | 24 |
| Filter outlet after 20 days | 5 | 76 |
| Distilled water | 3 | — |

A second test (documented in table 5 below) was conducted making a filtering element, containing approximately 60 g of material according to the present invention, at the inlet of a coffee machine, with mixed water-steam cycle.

The tests were conducted, using 4 different samples, with standard chemical water at 35° f.

TABLE 5

Second hardness reduction test, coffee machine
with standard chemical water
(The values were determined according to the method ASTM D513)

| Processed water (l) | Sample 1 (no filter) Reduction % | Sample 2 Reduction % | Sample 3 Reduction % | Sample 4 Reduction % |
|---|---|---|---|---|
| 0 | 0 | 35 | 42 | 57 |
| 8 | 36 | 70 | 68 | 77 |
| 43 | 42 | 77 | 74 | 74 |
| 96.5 | 32 | 68 | 74 | 79 |

The mean hardness reduction, in this second test, is thus approximately 66%.

A third test (documented in table 6 below) was conducted making a filtering element, containing approximately 60 g of material according to the present invention, at the inlet of a coffee machine, with mixed water-steam cycle.

The tests were conducted, using 4 different samples, with pipeline water at 28° f, fixed residue 270 mg/l.

TABLE 6

Third hardness reduction test, coffee machine with pipeline water
(The values were determined according to the method ASTM D513)

| Processed water (l) | Sample 1 (no filter) Reduction % | Sample 2 Reduction % | Sample 3 Reduction % | Sample 4 Reduction % |
|---|---|---|---|---|
| 0 | 11 | 46 | 32 | 32 |
| 50 | 0 | 67 | 14 | 11 |
| 100 | 24 | 43 | 47 | 43 |
| 200 | 32 | 51 | 55 | 47 |

The mean reduction in hardness, in this third test, is thus approximately 35%.

Similar performance was obtained using a filtering element at the input to other electrical appliances, e.g. irons or washing machines.

A fourth test (documented in table 7 below) was carried out using a filtering element containing 7 kg of material according to the present invention, connected to the water supply pipeline at the input to a washing machine, which carried out a complete wash cycle per day. Since a wash cycle corresponds to approximately 15 lt of water used, the test had a duration of 15 months. Both the processed litres, and the duration over time highlight that the invention is innovative, also with respect to the prior art, because the catalyst supported by the polymeric base is effectively active, well beyond the limits highlighted in the literature.

TABLE 7

Fourth hardness reduction test, washing machine with pipeline water
(The values were determined according to the method ASTM D513)

| Sample | Volume (l) | Scale reduction (%) |
|---|---|---|
| Filter outlet flow rate 4.8 l/m | 2000 | 40 |
| Filter outlet flow rate 2 l/m | 7000 | 51 |
| Filter outlet flow rate 3 l/m | 7000 | 41 |

This test, too, provides very interesting scale reduction values.

In addition, duration tests were carried out, applied to machines for the preparation of hot drinks (coffee) using a kit K. The quantity ratio of the kit K was 15 gr of material C in 1 lt of water at 45° F. hardness.

The machines for the preparation of hot drinks were selected among those available on the market, both among models that use pods and models that use capsules.

The test was conducted determining the total volume of water dispensed by the machines before the boiler shut down, causing the operation of the machine to be stopped. The test was conducted dispensing 50 ml of water from the machine and a subsequent pause of 5 minutes; this procedure is defined as a cycle. As shown in table 8, the duration of the test with the KIT has a duration of more than 25 days, during which the support with enzyme maintains its effectiveness. The persistent effectiveness is a characteristic part of the object of the invention, inasmuch as it is well known that enzymes are subject to a very fast reduction of their activity, when they are placed in an aqueous solution or in contact therewith (N. U. Medrum and F. J. W. Roughton, "*Carbonic anhydrase. Its preparation and properties*", Physiological and Biochemical Laboratories, Cambridge., received Aug. 2, 1933).

TABLE 8

Fifth hardness reduction test, coffee machines

| TYPE OF COFFEE MACHINE | WATER HARDNESS IN FRENCH DEGREES | VOLUME OF WATER DISPENSED UNTIL SHUT-DOWN | NUMBER OF COFFEES DISPENSED (50 ml) | INCREASE IN THE VOLUME OF WATER USED AS A RESULT OF THE USE OF THE KIT K |
|---|---|---|---|---|
| CAPSULE COFFEE MACHINE WITH KIT K in concentration of 15 gr of material C with respect to water. | 45 | 345 | 6900 | 137.93% |

TABLE 8-continued

Fifth hardness reduction test, coffee machines

| TYPE OF COFFEE MACHINE | WATER HARDNESS IN FRENCH DEGREES | VOLUME OF WATER DISPENSED UNTIL SHUT-DOWN | NUMBER OF COFFEES DISPENSED (50 ml) | INCREASE IN THE VOLUME OF WATER USED AS A RESULT OF THE USE OF THE KIT K |
|---|---|---|---|---|
| CAPSULE COFFEE MACHINE | 45 | 145 | 2900 | |
| POD COFFEE MACHINE WITH KIT K in concentration of 15 gr of material C with respect to water. | 45 | 135.1 | 2702 | 187.45% |
| POD COFFEE MACHINE | 45 | 47 | 940 | |

As pointed out above in several parts, an important advantageous aspect of the present, invention is the obtainment of satisfactory results with a very small amount of material.

As stated, the kit K is revealed to be effective using an amount of material, per litre of treated water, between 0.1 g and 60 g, preferably between 1 g and 15 g, still more preferably between 5 g and 15 g.

If a 15 g sachet is used in one litre of water, the ratio between material and liquid is 1.5% p/p.

More in general, the weight percentage of the kit K relative to the volume of the container containing the treated liquid is between 0.1% and 5%.

Preferably, this percentage is between 1% and 3%.

In the products currently on the market, the weight ratios between material and liquid are indicated below.

With regard to filters, considering that they are filled with polymeric material and water is forced to traverse them, the average ratio between material and water is, in the best of cases, 50%.

With regard instead to the sachets containing resins, the smallest one currently present on the market weighs 50 g, and it is recommended for a maximum quantity of liquid of approximately 2 litres: hence—in the maximum case—the ratio between material and treated liquid is 25%.

With regard to the effectiveness of the use of such amount of material, reference is made in particular to Table 1 and to Table 8.

To further clarify the advantageous aspects of the present invention, the characteristics of a product available on the market are briefly illustrated.

This product, too, is supplied in the form of a sachet containing the suitable material for the reduction of the content of unwanted substances in a liquid.

The data supplied by the manufacturer indicate that with water hardness of 45°f, the sachet used (which has a material/liquid weight ratio of 25%) has a duration of 90 litres of water, whilst the kit K according to the present invention (which instead has a material/liquid ratio of 1.5%) has a duration of over 180 litres, as indicated in Table 8 and in other tables.

Therefore, to summarise, the weight percentages of the material used for the reduction of unwanted substances, with respect to the quantity of treated liquid are, in the various types of products available on the market, the ones indicated in the following table 9.

TABLE 9

Quantity of material used in the solutions available on the market

| Type of product | Quantity of material used | Quantity of liquid treated | % in weight material/treated liquid |
|---|---|---|---|
| Kit K according to the invention | 15 g | 345 l | 0.004348% |
| Sachet with resins | 50 g | 90 l | 0.056% |
| Filter with ion-exchange resin | 400 g | 100 l | 0.04% |
| Polyamide filter with enzymatic catalyst | 60 g | 300 l | 0.03% |

Hence, it is altogether evident that the kit K according to the present invention makes it possible to obtain excellent results, on the treated liquid, using a percentage in weight of material that is lower, by at least one order of magnitude, than the other solutions currently available on the market, with considerable advantages from the economic viewpoint and also in terms of environmental impact.

The innovative and advantageous aspects of the present invention are further highlighted by the considerations that follow.

The liquids treatable with the material according to the present invention (or with the kit K according to the present invention) normally have a pH value above 6.

It is well known from the scientific literature (see, for example, Seymour H. Koenig and Rodney D. Brown III, "$H_2CO_3$ as substrate for carbonic anhydrase in the dehydration of $HCO_3^-$", Proc. Nat. Acad. Sci. USA, Vol. 69, No. 9, pp. 2422-2425, September 1972) that as pH increases—in particular for pH values between 6 and 8—the ratio and the velocity of interconversion of the hydration reaction ($CO_2 \rightarrow HCO_3^-$) increase, while the same parameters for the dehydration reaction decrease ($HCO_3^- \rightarrow CO_2$).

In other words, the bond between $HCO_3^-$ and enzyme is too weak to be determined, and hence the enzyme itself has no effect on the velocity and on the amount of bicarbonates/carbonates converted into $CO_2$.

Other literature confirms the same conclusions, i.e. that the carbonic anhydrase enzyme tends to promote the hydration reaction of $CO_2$, and facilitates the precipitation of $CaCO_3$ (Parissa Mirjafari et al., "Investigating the application of enzyme carbonic anhydrase for $CO_2$ sequestration purposes", Ind. Eng. Chem. Res. 2007, 46, 921-926).

It is also known that (F. J. W. Roughton and V. H. Booth (Ramsay Memorial Fellow), *The Effect of Substrate Concentration, pH and other Factors upon the Activity of Carbonic Anhydrase*—, Physiology Laboratory, University of Cambridge, England and the Fatigue Laboratory, Harvard University, Boston, Mass., U.S.A.) $SO_4^{2-}$, $Cl^-$, $Br^-$, $NO3^-$ ions and other anions of carboxylic acids have inhibition effects on the activity of the carbonic anhydrase enzyme.

Other substances like Silver, Zinc, etc. (N. U. Medrum and F. J. W. Roughton, "*Carbonic anhydrase. Its preparation and properties*", Physiological and Biochemical Laboratories, Cambridge., received Aug. 2, 1933) are deactivators of the enzyme and, like for the aforementioned anions, the salts of these metals can also be commonly present in industrial and household water.

Since the water, be it industrial or household, contains these anions, it did not appear at all obvious, in the applicant's view, that the material of the present invention would maintain its effectiveness in reducing the unwanted substances (including carbonate and/or hydrogen carbonate salts) for such a long time and for such large volumes of water.

Therefore, thanks to the features of the present invention—and as confirmed by the experimental results—the carbonic anhydrase enzyme (in a wholly opposite manner to what the state of the art would lead to expect) is able to generate such an amount of $CO_2$—even if minimal—as to determine an overall reduction in $CaCO_3$.

Another non-obvious aspect of the present invention is that the enzymes still maintain a certain activity even if they are immobilised on the surface of the polymeric and/or inorganic base.

It is well known that enzymes can be subject to degradation over time, and it is also known that the enzymes immobilisation does not promote their activity, in fact it tends to penalise it.

Thanks to the solution employed in the present invention, the immobilisation of enzymes on the polymeric and/or inorganic base promotes their stabilisation, and hence they are subject, in a very reduced way, to undergo degradation over time. Hence, stabilised enzymes can for example have a longer shelf life.

While on one hand, as stated, the immobilisation of enzymes tends to reduce their activity, the solution of the present invention has made it possible to reach an optimal compromise between stability and activity of the enzymes: the latter, therefore, maintain for a long period of time such a level of activity as to generate such a quantity of $CO_2$ as to determine an overall reduction in $CaCO_3$.

The present invention further relates to a method for reducing the contents of polluting and/or unwanted substances in a container containing a liquid comprising water.

The method comprises a step of providing at least one kit K comprising at least a wrapper B permeable to water and to the substances dissolved therein, containing a plurality of spherical, or substantially spherical bodies C, each comprising a polymeric base on which is immobilised a predetermined quantity of an enzyme selected in the sub-group of carbonic anhydrase.

The method further provides a step of immersing the kit K in the aforesaid container.

This step is followed by a step of allowing the kit K act within the aforesaid container for a period of time.

It has been observed experimentally that the kit K starts acting after as little as 10 minutes.

The spherical or substantially spherical bodies C have maximum dimension between 2.5 mm and 3.5 mm.

In a preferred embodiment of the invention, the bodies C have maximum dimension of approximately 3 mm.

The weight percentage of the kit K with respect to the treated liquid is between 0.2% and 5%; preferably, this weight percentage is between 1% and 3%.

The total weight of the bodies C contained within the wrapper is between 1 g and 60 g, preferably between 1 g and 15 g, still more preferably between 5 g and 15 g.

In an embodiment of the invention of particular practical interest, the weight of the bodies C contained within the wrapper is approximately 15 g.

The enzyme is present, on the body C, in a concentration between 0.0001% and 30%, and more preferably between 0.005% and 1%, percentages referred to the total weight of the polymeric base.

In an embodiment of the invention of particular practical interest, the liquid to be treated is contained in a container.

For example, this container can consist of the tank of an electrical appliance, of any type or dimensions.

Within this tank, the liquid can be still, or in cyclic motion, but not changed, replaced except after a certain predetermined period of time.

The present invention has been described according to preferred embodiments, but equivalent variants can be conceived without thereby departing from the scope of protection offered by the claims that follow.

The invention claimed is:

1. A kit for reducing a content of polluting and/or unwanted substances in a liquid, comprising:
at least a wrapper containing a plurality of bodies, each of said plurality of bodies including at least a portion made of a material comprising:
at least a polymeric and/or inorganic base, suitable to be immersed in said liquid, having at least a surface, whereto is bonded at least one catalyst of a degradation reaction of inorganic salts in gaseous substances,
wherein said catalyst, whose function is to reduce energy required for activation of said reaction and to accelerate progress of said reaction, being an enzyme selected among a lyase group, a hydrolase group and an oxidoreductase group,
wherein said wrapper is permeable to water and substances dissolved in the water, and wherein said wrapper is intended to be immersed in a container of the liquid to be treated.

2. The kit according to claim 1, wherein said body has a spherical or substantially spherical shape, and wherein said body has a maximum dimension between 0.1 μm and 5 mm.

3. The kit according to claim 1, wherein said body has a maximum dimension between 2.5 mm and 3.5 mm.

4. The kit according to claim 1, wherein said body has a maximum dimension of about 3 mm.

5. The kit according to claim 1, wherein said catalyst is bonded to said surface of said polymeric and/or inorganic base in a covalent or crosslinked way.

6. The kit according to claim 1, wherein said catalyst is an enzyme selected in the group of lyases.

7. The kit according to claim 1, wherein said polymeric base is made of poly amide.

8. The kit according to claim 1, wherein said polymeric and/or inorganic base is included in a body suitable to be immersed in the container of the liquid to be treated, so as to initiate the activity of said catalyst by simple contact, without stirring and without forced fluid. circulation.

9. The kit according to claim 1, comprising said catalyst in a concentration comprised between 0.0001% and 30%, wherein the percentages refer to the total weight of said polymeric base.

10. A method for reducing content of polluting and/or unwanted substances in a liquid, comprising the steps of:
provide at least a kit comprising at least a wrapper permeable to water and to the substances dissolved therein, comprising a plurality of spherical, or substantially spherical bodies, each of the plurality of bodies comprising a polymeric base on which is immobilised a predetermined quantity of an enzyme selected in the sub-group of carbonic anhydrase;
immersing said kit in said liquid; and
allowing said kit to act within a container for a period of time.

11. The method according to claim 10, wherein said spherical, or substantially spherical, bodies have a maximum dimension between 2.5 mm and 3.5 mm.

12. The method according to claim 10, wherein the weight percentage of said kit with respect to the treated liquid is between 0.1% and 5%.

13. The method according to claim 12, wherein the weight percentage of said kit with respect to the treated liquid is between 1% and 3%.

14. The method according to claim 10, wherein the total weight of said bodies contained within said wrapper is between 1 g and 60 g.

15. The method according to claim 10, wherein the total weight of said bodies contained within said wrapper is between 1 g and 15 g.

16. The method according to claim 10, wherein the total weight of said bodies contained within said wrapper is between 5 g and 15 g.

17. The method according to claim 10, further comprising said enzyme in a concentration between 0.0001% and 30%, and wherein the percentages refer to the total weight of the polymeric base of each of said bodies.

* * * * *